(12) United States Patent
Ghanam et al.

(10) Patent No.: US 12,279,836 B2
(45) Date of Patent: Apr. 22, 2025

(54) TRACKER WITH SWITCHABLE RADIATION CHARACTERISTICS

(71) Applicant: Stryker European Operations Limited, Carrigtwohill (IE)

(72) Inventors: Fadi Ghanam, Schallstadt (DE);
Fabian Riegelsberger, Umkirch (DE);
David Hofmann, Freiburg (DE);
Reinhold Zimmermann, Freiburg (DE); Andreas Reutter, Berlin (DE)

(73) Assignee: Stryker European Operations Limited, Carrigtwohill (IE)

(*) Notice: Subject to any disclaimer, the term of this patent is extended or adjusted under 35 U.S.C. 154(b) by 0 days.

(21) Appl. No.: 18/545,299

(22) Filed: Dec. 19, 2023

(65) Prior Publication Data

US 2024/0115328 A1  Apr. 11, 2024

Related U.S. Application Data

(63) Continuation of application No. 17/546,411, filed on Dec. 9, 2021, now Pat. No. 11,883,116.

(30) Foreign Application Priority Data

Dec. 10, 2020  (EP) .................................... 20213089

(51) Int. Cl.
| | | |
|---|---|---|
| A61B 5/00 | (2006.01) | |
| A61B 34/00 | (2016.01) | |
| A61B 34/20 | (2016.01) | |

(52) U.S. Cl.
CPC .............. *A61B 34/20* (2016.02); *A61B 34/76* (2016.02); *A61B 2034/2051* (2016.02)

(58) Field of Classification Search
CPC .. A61B 34/20; A61B 34/76; A61B 2034/2051
See application file for complete search history.

(56) References Cited

U.S. PATENT DOCUMENTS

| | | |
|---|---|---|
| 9,179,984 B2 | 11/2015 | Teichman et al. |
| 9,220,573 B2 | 12/2015 | Kendrick et al. |
| (Continued) | | |

FOREIGN PATENT DOCUMENTS

| | | |
|---|---|---|
| EP | 3556316 A1 | 10/2019 |
| EP | 3725256 A1 | 10/2020 |
| (Continued) | | |

*Primary Examiner* — Joel F Brutus
(74) *Attorney, Agent, or Firm* — Howard & Howard Attorneys PLLC

(57) ABSTRACT

A tracker, a surgical navigation system with the tracker, and a method of operating the tracker are described. The tracker comprises a first switch configured to be operated between a first switch configuration and a second switch configuration. The tracker also comprises one or more sources of electromagnetic radiation configured to selectively emit electromagnetic radiation with a first radiation characteristic or a second radiation characteristic. The tracker further comprises electrical circuitry configured to selectively control the one or more sources of electromagnetic radiation to emit electromagnetic radiation having the first radiation characteristic in the first switch configuration and to emit electromagnetic radiation having the second radiation characteristic in the second switch configuration, wherein the second radiation characteristic is different from the first radiation characteristic.

19 Claims, 12 Drawing Sheets

(56) References Cited

U.S. PATENT DOCUMENTS

| | | | |
|---|---|---|---|
| 2005/0288575 A1* | 12/2005 | de la Barrera | A61B 34/20 |
| | | | 600/423 |
| 2017/0340406 A1 | 11/2017 | Hendriks et al. | |
| 2019/0142525 A1* | 5/2019 | Malackowski | G01S 17/86 |
| | | | 398/115 |
| 2019/0321108 A1 | 10/2019 | Ghanam et al. | |
| 2020/0069376 A1 | 3/2020 | Garcia et al. | |
| 2022/0183769 A1 | 6/2022 | Ghanam et al. | |

FOREIGN PATENT DOCUMENTS

| | | |
|---|---|---|
| EP | 3725257 A1 | 10/2020 |
| WO | 2008103272 A2 | 8/2008 |
| WO | 2017004029 A1 | 1/2017 |
| WO | 2018032084 A1 | 2/2018 |

* cited by examiner

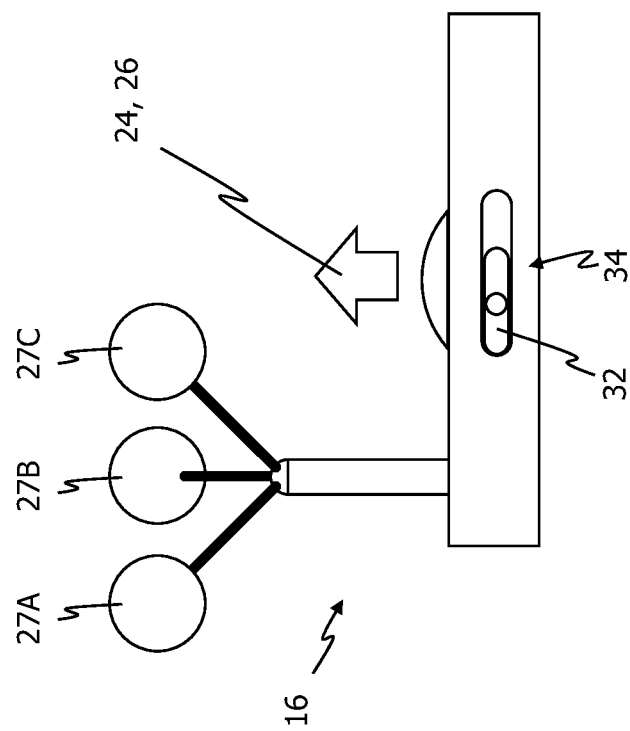
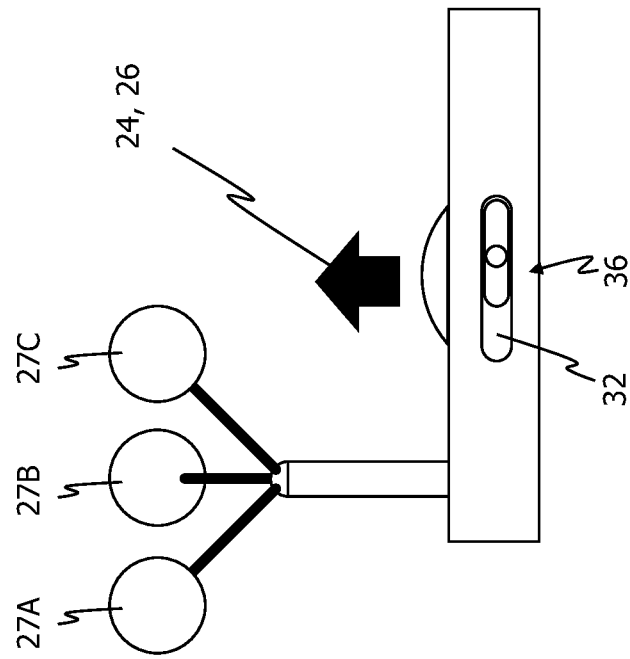
Fig. 3A
Fig. 3B

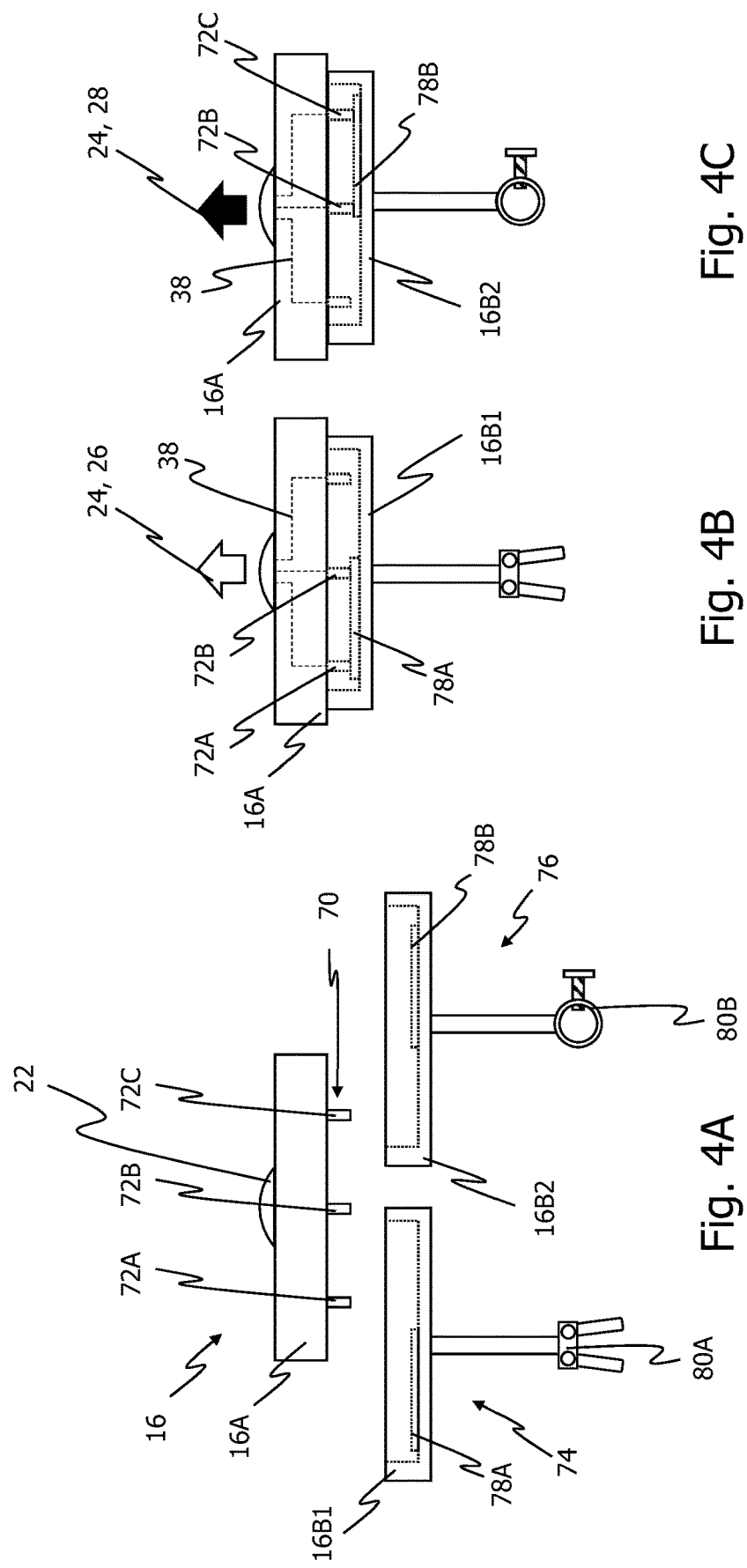

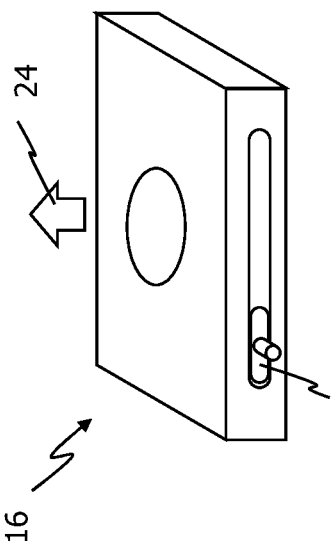
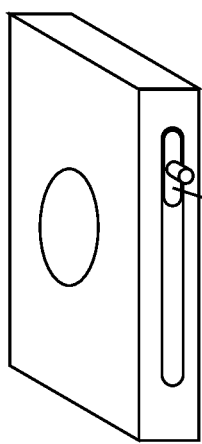
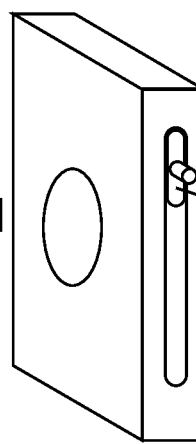
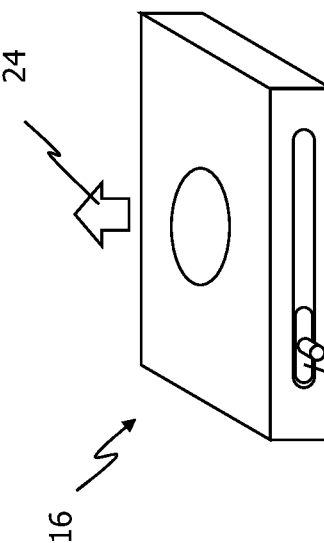
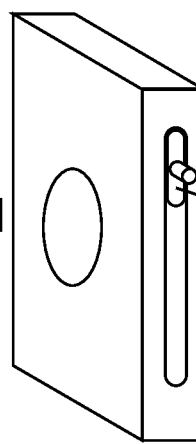

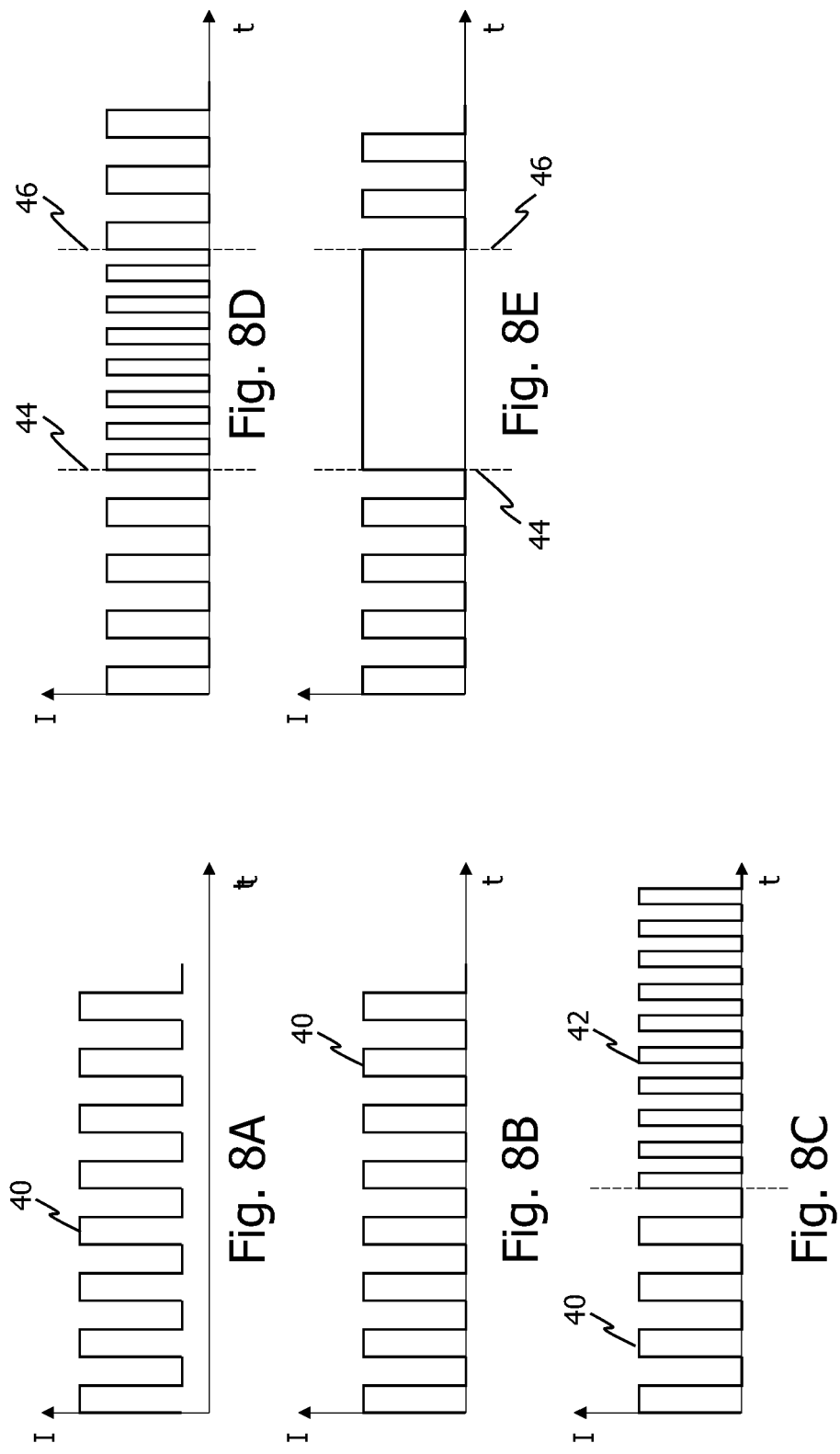

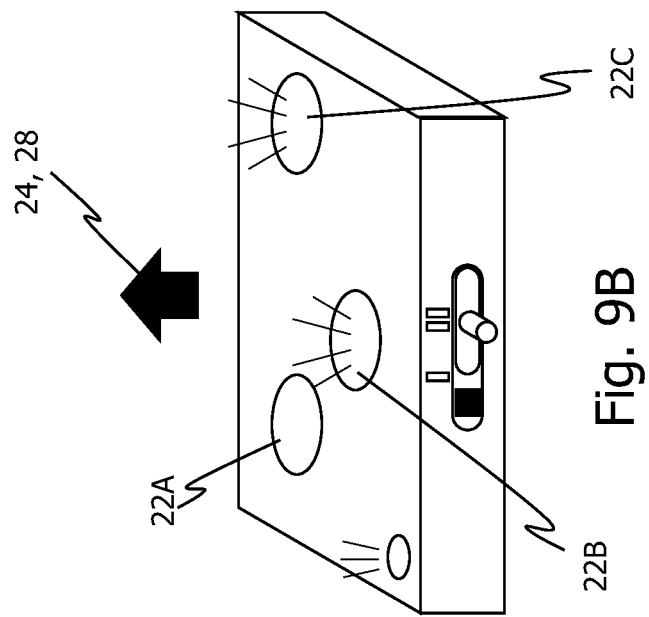
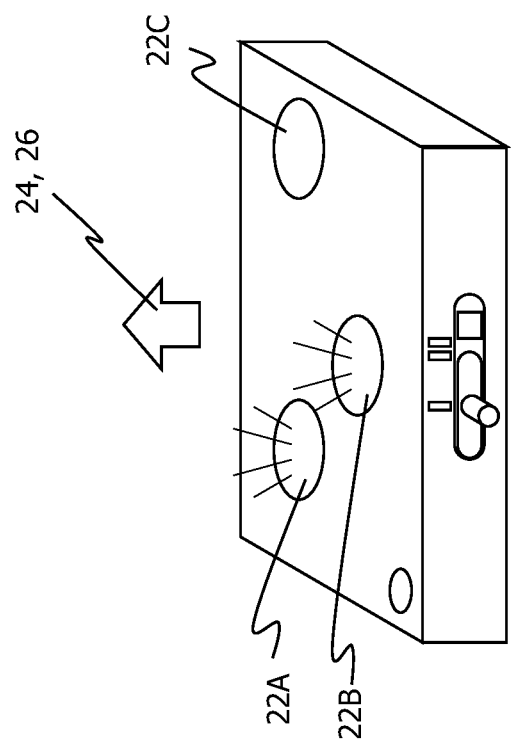
Fig. 9B
Fig. 9A

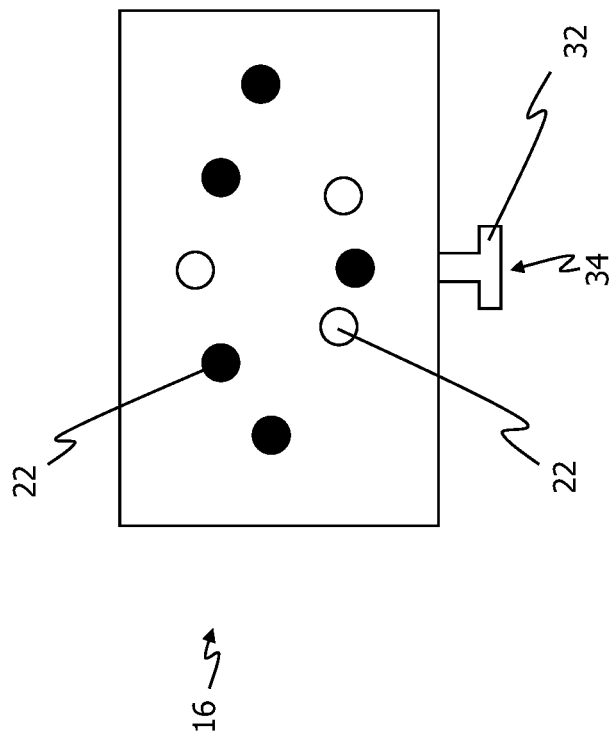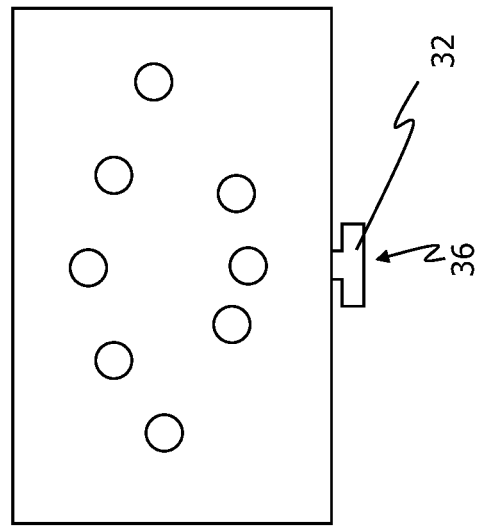

TRACKER WITH SWITCHABLE RADIATION CHARACTERISTICS

PRIORITY CLAIM

This is a continuation of U.S. application Ser. No. 17/546,411, filed on Dec. 9, 2021, which claims priority under 35 U.S.C. § 119 to European Patent Application No. 20213089.4, filed on Dec. 10, 2020, the entire contents of each being hereby incorporated by reference.

TECHNICAL FIELD

The present disclosure generally relates to tracker, for example in the context of surgical navigation. In particular, a tracker with switchable radiation characteristics, a surgical navigation system comprising the tracker, and a method of operating the tracker are presented.

BACKGROUND

Surgical navigation systems are typically configured to track surgical objects such as a surgical instrument or a patient. A common tracking technique involves a tracker with a source of electromagnetic radiation as well as an optical sensor capable of detecting the electromagnetic radiation emitted by the tracker. Based on the detected electromagnetic radiation, information on one or both of a position and an orientation of the tracker can be determined.

During a surgical procedure, the surgeon may want to communicate with the surgical navigation system, but typical user interfaces such as a keyboard and a mouse may be arranged at an inconvenient distance or inconvenient place. Moreover, such user interfaces pose a contamination risk for a sterile surgery environment. Especially communication with the surgical navigation system for calibrating or operating the tracker may be time consuming and result in contamination of the sterile surgery environment.

The surgeon may disinfect his or her hands after having operated the user interface. However, such disinfecting procedures are time inefficient and strenuous.

SUMMARY

There is a need for a technique that solves one or more of the aforementioned or other problems.

According to a first aspect, a tracker for a surgical navigation system is provided. The tracker comprises a first switch configured to be operated between a first switch configuration and a second switch configuration. The tracker comprises one or more sources of electromagnetic radiation configured to selectively emit electromagnetic radiation with a first radiation characteristic or a second radiation characteristic. The tracker further comprises electrical circuitry configured to selectively control the one or more sources of electromagnetic radiation to emit electromagnetic radiation having the first radiation characteristic in the first switch configuration and to emit electromagnetic radiation having the second radiation characteristic in the second switch configuration, wherein the second radiation characteristic is different from the first radiation characteristic.

The first switch may be configured to be operated while the tracker is being tracked by the surgical navigation system. The first switch may be configured to be operated upon configuring (e.g., assembling) the tracker in preparation of a surgical procedure. The first switch may be user-operable.

The first switch, or any further switch, may be configured to be operated between more than two switch configurations, such as three, four, five, six, or more switch configurations. In such a case, one of the switch configurations may be configured to switch off the tracker (e.g., to switch off a power source integrated into the tracker).

The source of electromagnetic radiation may be configured to emit electromagnetic radiation with more than two radiation characteristics, such as two, three, four, five, or more radiation characteristics.

The source of electromagnetic radiation may be a light emitting diode (LED), a polymer light emitting diode, a laser, an incandescent light bulb, or a fibre cable (e.g., an end face or side face thereof) coupled to a light source. The source of electromagnetic radiation may be configured to emit electromagnetic radiation in at least one of the visible light spectrum, the infrared light spectrum, and the ultraviolet light spectrum.

The first radiation characteristic may comprise emission of electromagnetic radiation at a first operation frequency and the second radiation characteristic may comprise emission of electromagnetic radiation at a second operation frequency different from the first operation frequency. The first and second operation frequencies may each indicate a rate of a periodic intensity change of the electromagnetic radiation. The intensity of the electromagnetic radiation may change between a first intensity and a second intensity that is smaller than the first intensity. The second intensity may be zero or essentially zero. One of the first operation frequency and the second operation frequency may be zero with a continuous emission of electromagnetic radiation.

The first radiation characteristic may comprise emission of electromagnetic radiation having a first wavelength and the second radiation characteristic may comprise emission of electromagnetic radiation having a second wavelength different from the first wavelength. The first and second wavelengths may be in a visible light spectrum. Alternatively, the first and second wavelengths may be in an infrared light spectrum. Further alternatively, one of the first and second wavelengths may be in the visible light spectrum and the other one of the first and second wavelengths may be in the infrared light spectrum.

The tracker may comprise a plurality of sources of electromagnetic radiation, such as two, three, four, five, or more sources of electromagnetic radiation. In such a case, changing between the first and second radiation characteristics of the plurality of sources of electromagnetic radiation may comprise at least one of (i) at least one of the sources of electromagnetic radiation starting emitting electromagnetic radiation and (ii) at least one of the sources of electromagnetic radiation stopping emitting electromagnetic radiation. A first subset of sources of electromagnetic radiation may comprise exactly two sources of electromagnetic radiation. In some implementations, in the first radiation characteristic only one source of the first subset is configured to emit electromagnetic radiation, and in the second radiation characteristic only the other source of the first subset is configured to emit electromagnetic radiation.

In case the tracker comprises a plurality of sources of electromagnetic radiation as described above, a second switch may be configured to be operated between a third switch configuration and a fourth switch configuration. A, or the, first subset of the plurality of sources of electromagnetic radiation may be assigned to the first switch, and a second subset of the plurality of sources of electromagnetic radiation may be assigned to the second switch. The first subset of the plurality of sources of electromagnetic radiation may be configured to selectively emit electromagnetic radiation having a first partial radiation characteristic or a second partial radiation characteristic. The second subset of the plurality of sources of electromagnetic radiation may be configured to selectively emit electromagnetic radiation having a third partial radiation characteristic or a fourth partial radiation characteristic. The first and second switches may be configured to be operated to only change the partial radiation characteristic of each assigned subset of sources of electromagnetic radiation.

The tracker may comprise an indicator configured to provide a first indication in the first switch configuration and a second indication in the second switch configuration. The first and second indications may be at least one of optically and haptically distinguishable for a user. The one or more sources of electromagnetic radiation may in particular be configured to emit infrared radiation. The indicator may comprise an indicator light source configured to emit visible light perceivable by the human eye. The indicator may comprise a switch position indicator configured to assign a first position of the first switch to the first switch configuration and to assign a second position of the first switch to the second switch configuration.

The first switch may be pre-configured to assume the first switch configuration and adapted to switch from the first to the second switch configuration only for a duration that the first switch is operated or for a fixed time duration after the first switch was operated. The first switch may be a spring-biased switch (e.g., a push button switch).

The tracker may comprise at least one powering component configured to provide power to the one or more sources of electromagnetic radiation, such as a power source (e.g., one or more button cell batteries) and/or a wireless power reception device. The power source may comprise two, three, four, or more button cell batteries. The power source may comprise a CR2032 and/or a CR2025 type button cell battery.

The tracker may comprise one or more passive tracking elements configured to reflect electromagnetic radiation. The tracker may comprise two, three, four, five, six, or more passive tracking elements. The one or more passive tracking elements may be configured to reflect predominantly visible light or infrared light. The one or more passive tracking elements may comprise reflective spheres.

The tracker may have more than two switch configurations. In some variants, the one or more sources of electromagnetic radiation may be configured to selectively emit electromagnetic radiation with a number of radiation characteristics at least equal to the number of switch configurations, wherein each of the switch configurations may be assigned to one of the radiation characteristics. For example, the tracker may have three switch configurations each assigned to one of three radiation characteristics, or the tracker may have four switch configurations each assigned to one of four radiation characteristics.

The first switch (and/or, optionally, a second switch) may comprise a mechanical switch configured to be operated by a user (e.g., while the tracker is being tracked). The mechanical switch may comprise one or more elements movable by the user to change the switch configuration. The switch may comprise a push button. The switch may comprise a sliding portion configured to be slid parallel to a tracker surface.

The first switch may comprise a first switch portion, a second switch portion configured to be electrically coupled to the first switch portion, and a third switch portion configured to be electrically coupled to the first switch portion.

In some variants, the first switch is in the first switch configuration when the second switch portion is electrically coupled to the first switch portion and in the second switch configuration when the third switch portion is electrically coupled to the first switch portion.

The tracker may comprise a first tracker part and at least one second tracker part that is at least one of movable relative to and removable from the first tracker part, wherein the first switch portion is provided at the first tracker part and the second switch portion and the third switch portion are collectively or individually provided at the at least one second tracker part. As an example, the second switch portion may be provided at one second tracker part and the third switch portion may be provided at another second tracker part. Alternatively, both the second and third switch portion may be provided at a single second tracker part. The first tracker part and a dedicated second tracker part may be configured to selectively assume a first relative position to realize the first switch configuration and a second relative position to realize the second switch configuration. The different relative positions may be defined by one or both of rotatory relative positions and translatory relative positions.

One of the first and the at least one second tracker part may carry the one or more sources of electromagnetic radiation. The other of the first and the at least one second tracker part may comprise an interface for coupling the tracker to an object that is to be tracked.

According to a second aspect, a surgical navigation system is provided. The surgical navigation system comprises the tracker described herein and an optical sensor capable of detecting different radiation characteristics of the tracker. The surgical navigation system further comprises a processor configured to selectively identify the first or second switch configuration based on the radiation characteristic detected by the optical sensor.

The processor may be configured to selectively identify the first or second switch configuration based on a comparison between the detected radiation characteristic and a predetermined radiation characteristic.

The processor may be configured to assign a first tracking mode to the first switch configuration and a second tracking mode to the second switch configuration. The first and/or second tracking modes may be assigned to an instrument and/or a patient. The first and/or second tracking modes may be assigned to different body parts of the patient.

The processor may be configured to identify a switching between the first and second switch configuration. The processor may be configured to determine a command issued by a user based on the identified switching between the first and second switch configuration. The processor may be configured to control a navigation procedure based on the command thus determined.

The optical sensor may be a camera, such as a mono camera or a stereo camera. In the case that the first radiation characteristic comprises emission of electromagnetic radiation at a first operation frequency and the second radiation characteristic comprises emission of electromagnetic radiation at a second operation frequency different from the first operation frequency as described above, the optical sensor may be a camera having a frame rate that is at least two times larger than a larger one of the first and second operation frequencies of the tracker.

In the case that the tracker comprises one or more passive tracking elements configured to reflect electromagnetic radiation, the optical sensor may be configured to detect electromagnetic radiation reflected by the one or more passive tracking elements.

According to a third aspect, a method for operating a tracker for a surgical navigation system is provided. The tracker comprises a first switch configured to be operated between a first switch configuration and a second switch configuration, one or more sources of electromagnetic radiation, electrical circuitry configured to selectively control the one or more sources of electromagnetic radiation to emit electromagnetic radiation with a first radiation characteristic or a second radiation characteristic, wherein the second radiation characteristic is different from the first radiation characteristic. The method may comprise providing power to the one or more sources of electromagnetic radiation. The method further comprises emitting, by the one or more sources of electromagnetic radiation, electromagnetic radiation having the first radiation characteristic in the first switch configuration and electromagnetic radiation having the second radiation characteristic in the second switch configuration.

According to a fourth aspect, a computer program product is provided, wherein the computer program product comprises program code portions configured to perform the method described herein when executed by a processor. The computer program product may be stored on a computer-readable recording medium. The computer-readable recording medium may be a non-transitory recording medium, such as a hard drive, USB stick, or a compact disc.

BRIEF DESCRIPTION OF THE DRAWINGS

Further details, advantages and aspects of the present disclosure will become apparent from the following embodiments taken in conjunction with the drawings, wherein:

FIG. 3A shows an embodiment of a tracker with three passive tracking elements in a first switch configuration;

FIG. 3B shows the tracker of FIG. 3A in a second switch configuration;

FIG. 4A shows an embodiment of tracker with a first switch that comprises a first, second, and third switch portion;

FIG. 4B shows the first switch portion electrically coupled to the second switch portion;

FIG. 4C shows the first switch portion electrically coupled to the third switch portion;

FIG. 6A shows a tracker with three switch configurations each assigned one of three radiation characteristics, wherein the switch is in a first of three switch configurations;

FIG. 6B shows the tracker shown in FIG. 6A wherein the first switch is in a second of three switch configurations;

FIG. 6C shows the tracker shown in FIG. 6A wherein the first switch is in a third of three switch configurations;

FIG. 6D shows a tracker with three switch configurations, wherein the first switch is in a first switch configuration assigned to a first radiation characteristic;

FIG. 6E shows the tracker shown in FIG. 6D, wherein the first switch is in a second switch configuration assigned to a second radiation characteristic;

FIG. 6F shows the tracker shown in FIG. 6D, wherein the first switch is a third switch configuration configured to turn off the tracker;

FIG. 8A shows an intensity of the electromagnetic radiation of a first operation frequency;

FIG. 8B shows an intensity of the electromagnetic radiation of a first operation frequency, wherein the intensity alternates between an intensity of zero and an intensity that is larger than zero;

FIG. 8C shows a change of the intensity of the electromagnetic radiation from a first operation frequency to a second operation frequency;

FIG. 8D shows a first change of the intensity of the electromagnetic radiation from a first operation frequency to a second operation frequency followed by a second change of the intensity back to the first operation frequency;

FIG. 8E shows an intensity of electromagnetic radiation during a continuous emission;

FIG. 9A shows an embodiment of a tracker with a plurality of sources of electromagnetic radiation FIG. 9B shows the tracker shown in FIG. 9A wherein the sources of electromagnetic radiation stop, continue, or start emitting electromagnetic radiation;

FIG. 10A shows another embodiment of a tracker, wherein three out of eight sources of electromagnetic radiation emit electromagnetic radiation;

FIG. 10B shows the tracker shown in FIG. 10A, wherein all sources of electromagnetic radiation emit electromagnetic radiation;

DETAILED DESCRIPTION

The tracker described herein may be used for any tracking technology involving emission of electromagnetic radiation, such as motion capture technology and tracking of virtual reality headsets. In the following, the tracker is described in the context of a surgical navigation system, but it should be understood that the tracker is not limited thereto.

Figure 1:
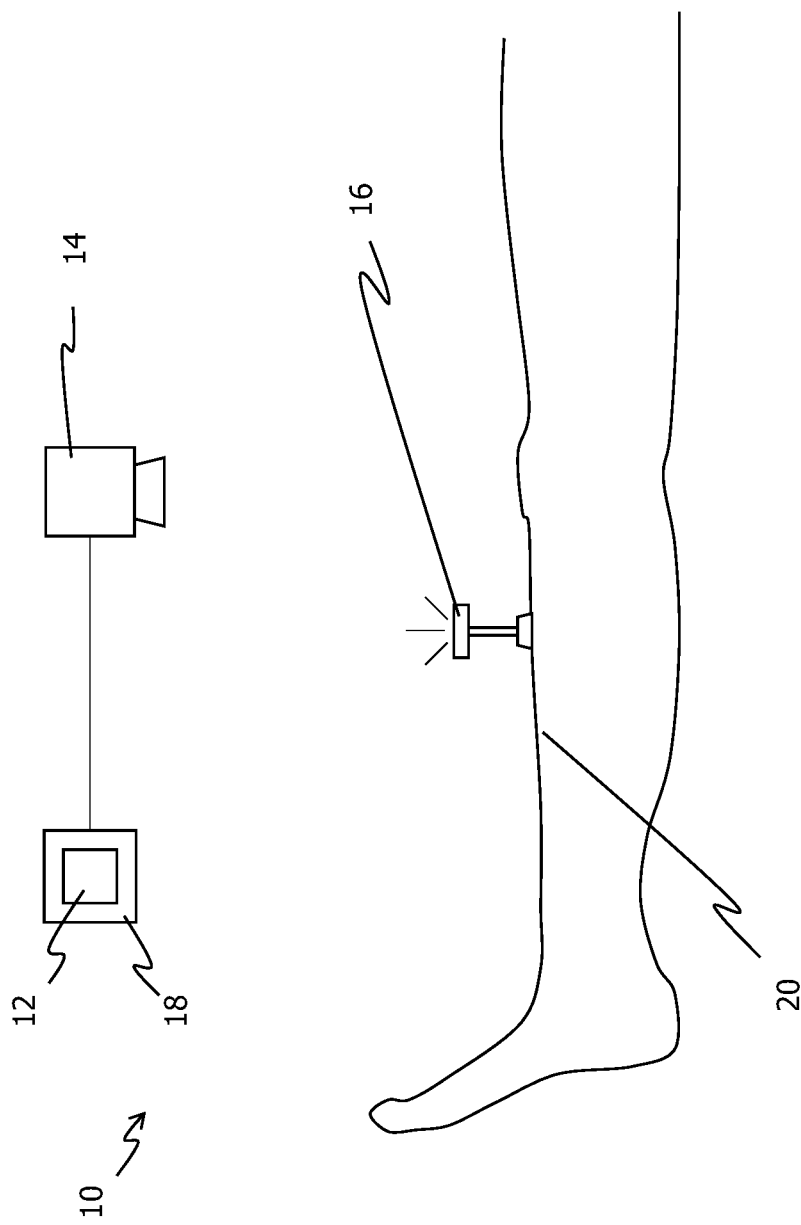
FIG. 1 shows an embodiment of a surgical navigation system comprising a processor, an optical sensor, and a tracker.

FIG. 1 schematically shows a surgical navigation system 10 comprising a processor 12, an optical sensor 14, and a tracker 16. The processor 12 is provided by a computer system 18. Alternatively, the processor 12 may be provided by a remote server or cloud computing resources.

The optical sensor 14 may be or may comprise a camera. The optical sensor 14 is configured to detect visible light and infrared light. Alternatively, the optical sensor 14 may be configured to detect at least one or any combination of at least one of visible light, infrared light, and ultraviolet light.

The tracker 16 comprises a mechanical interface for being coupled to a surgical object. The tracker 16 shown in FIG. 1 is coupled to a surgical object 20 in form of a skin area around a tibia of a patient. Alternatively the tracker 16 may be coupled to other regions of the patient, such as directly to the bone (e.g., the tibia) or an external element coupled to the patient (e.g., a table the patient is arranged on).

Figure 2B:
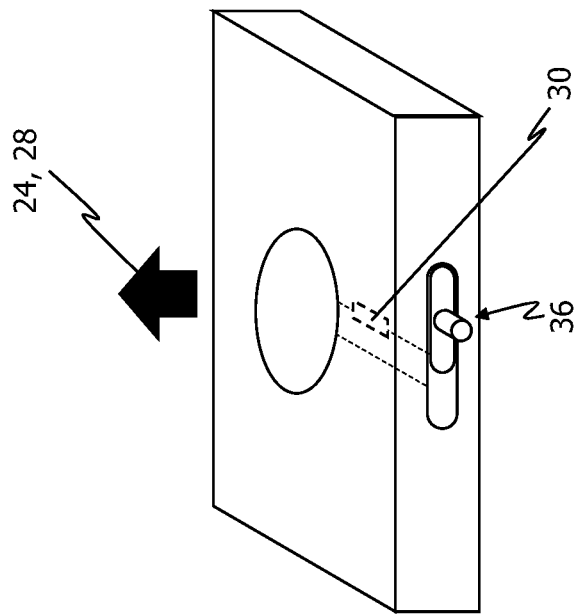
FIG. 2B shows a perspective view of the tracker shown in FIG. 2A in a second switch configuration.
Figure 2A:
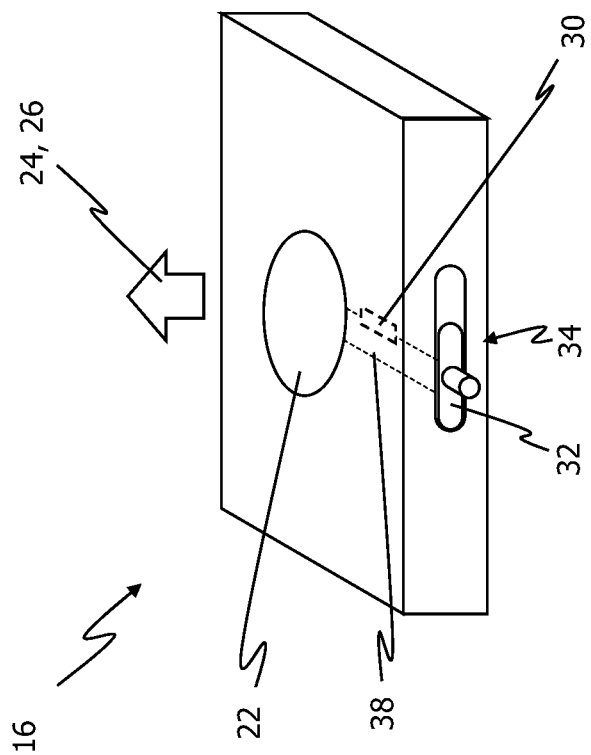
FIG. 2A shows a perspective view of an embodiment of a tracker in a first switch configuration.

FIG. 2A shows a perspective view of the tracker 16 in a schematic representation. The tracker 16 comprises at least one source 22 of electromagnetic radiation. For example, a single source 22 of electromagnetic radiation may be used for tracking a surgical instrument with only two freedoms of movement. In another realization, a plurality of trackers 16 each with a single source 22 of electromagnetic radiation may be individually coupled to a plurality of vertebra of the patient in order to track deformation of the spine. In other embodiments, the tracker may comprise a plurality of sources 22 of electromagnetic radiation, such as two, three, four or more. The tracker 16 may in particular comprise three or four (or more) such sources 22 so that the navigation system 10 can determine one or both of a position and an orientation of the tracker 16 in a coordinate system (e.g., of the optical sensor 14).

The source 22 of electromagnetic radiation shown in FIG. 2A is a light emitting diode (LED). Alternatively, the source 22 of electromagnetic radiation may be any other source capable of emitting electromagnetic radiation, such as an organic light emitting diode, a polymer light emitting diode, a laser, an incandescent light bulb, or a fibre cable coupled to an emitter of electromagnetic radiation. The source 22 of electromagnetic radiation may be configured to emit electromagnetic radiation in the visible light spectrum and/or infrared light spectrum. The optical sensor 14 of FIG. 1 is configured to detect at least a part of the spectrum of electromagnetic radiation emitted by the source 22 of electromagnetic radiation.

The tracker 16 can be tracked based on one or both of the electromagnetic radiation 24 emitted by the one or more sources 22 of electromagnetic radiation and electromagnetic radiation reflected by one or more passive tracking elements. As such, the tracker 16 may in some embodiments comprise one or more passive tracking elements configured to reflect electromagnetic radiation. FIG. 3A, B shows a variant of a tracker 16 with three passive tracking elements 27A-C. The tracker 16 may comprise any other number of passive tracking elements 27, such as one, two, four, or more passive tracking elements 27. The three passive tracking elements 27A-C each comprise a sphere configured to reflect electromagnetic radiation. The spheres may be configured to reflect predominantly or entirely a specific light spectrum such as visible light, infrared light or ultraviolet light.

The one or more sources 22 of electromagnetic radiation may be configured to emit electromagnetic radiation with a light spectrum (e.g., infrared light or visible light) for which the passive tracking elements 27 are reflective (e.g., a reflectance larger than 0.5, 0.7, or 0.9). The tracker 16 can therefore be tracked based on electromagnetic radiation originating from the sources 22 of electromagnetic radiation and the passive tracking elements 27. Alternatively, the one or more sources 22 of electromagnetic radiation may be configured to emit electromagnetic radiation with a light spectrum (e.g., infrared light or visible light) for which the passive tracking elements 27 are not or less reflective (e.g., a reflectance smaller than 0.1, 0.3, or 0.5). For such a tracker 16, reflections of the source 22 of electromagnetic radiation by the passive tracking elements 27 that can negatively affect tracking are reduced.

The tracker 16 further comprises a power source 30 configured to provide power to the source 22 of electromagnetic radiation. The power source 30 shown in FIG. 2A is a battery in form of a button cell (e.g., a CR2032 or CR2025 button cell). Alternatively, the battery may be a AA or AAA type cell. A tracker 16 with a smaller battery, such as a button cell, has a smaller weight. A tracker 16 with a larger battery commonly has a larger capacity for a longer operation time. The power source 30 may be a rechargeable battery such as a lithium ion battery. The power source 30 may comprise a single battery or a plurality of batteries, such as two, three, four, or more batteries. Alternatively or additionally, the power source 30 may comprise a power cord (e.g., to a power socket or an outlet of a nearby surgical device). In case a wireless power reception device is provided, the tracker 16 will be configured to receive power wirelessly.

The tracker 16 comprises a first switch 32 configured to be operated by a user between a first switch configuration 34 as shown in FIG. 2A and a second switch configuration 36 as shown in FIG. 2B.

The source 22 of electromagnetic radiation is configured to selectively emit electromagnetic radiation 24 with a first radiation characteristic 26 or a second radiation characteristic 28, wherein the first and second radiation characteristics 26, 28 are different from each other. The source 22 of electromagnetic radiation in the state illustrated in FIG. 2A (first switch configuration 34) emits electromagnetic radiation 24 with the first radiation characteristic 26 and the same source 22 of electromagnetic radiation in the state illustrated in FIG. 2B (second switch configuration 36) emits electromagnetic radiation 24 with the second radiation characteristic 26. In case two or more such sources 22 are provided, all of those sources 22 may collectively emit with the same (first or second) radiation characteristic. In other variants, only a true subset of one or more such sources 22 collectively emit with the same (first or second) radiation characteristic, while another true subset of such sources 22 emits with a radiation characteristic that, in some variants, is different from both the first and the second radiation characteristic.

The tracker 16 further comprises electrical circuitry 38 (only schematically shown in FIGS. 2A and 2B) configured to selectively control the source(s) 22 of electromagnetic radiation to emit electromagnetic radiation 24 having the first radiation characteristic 26 in the first switch configuration 34 and to emit electromagnetic radiation 24 having the second radiation characteristic 26 in the second switch configuration 36.

The first switch 32 shown in FIGS. 2A and 2B is an exemplary mechanically operable switch in form of a sliding switch that remains in a switch configuration after being operated. Therefore, the first switch 32 does not change autonomously from the first switch configuration 34 to the second switch configuration 36 (or vice versa). After moving the first switch 32 into a selected switch configuration, a user can work with the tracker 16 indefinitely in the selected switch configuration.

The first switch 32 may be spring-biased against an operation direction. As an example, the first switch 32 may alternatively be a push button. Such a push button does not require a sliding sideways movement and requires less space on a surface of the tracker 16. In such an implementation, the first and second switch configurations 34, 36 can be provided in two different variations as described in the following.

In the first variation, the push button alternates between the first and second switch configurations 34, 36 when being operated, but remains in a switch configuration after operation (commonly referred to as latching switch). Such a switch type remains in a switch configuration indefinitely.

In the second variation, the push button is biased towards one switch configuration (e.g., the first switch configuration) and only switches to the other switch configuration (e.g., the second switch configuration) for the duration that the user is operating the first switch 32 (commonly referred to as "momentary switch"). The user can therefore perform an input similar to a mouse-click, which requires only little physical interaction with the switch 32.

In a third variation, the push button is biased towards one switch configuration (e.g., the first switch configuration) and only switches to the other switch configuration (e.g., the second switch configuration) for a fixed time duration after the switch 32 was operated. The fixed time duration can be shorter than a manual input (e.g., shorter than 0.1 s, 10 ms, or 1 ms), which can reduce power consumption, or longer (e.g., longer than 0.1 s, 1 s, or 10 s) in order to ensure detection of the emitted electromagnetic radiation. A fixed time duration can improve input efficiency. Furthermore, the operation of the switch 32 may be identified by the fixed duration (in addition to the emitted first or second radiation characteristic), which increases input accuracy.

FIGS. 4A-C show another variant of a first switch 32 that comprises multiple switch portions at two tracker parts 16A and 16B1 or 16B2 that are removable from each other. The first switch 32 of FIGS. 4A-C comprises a first switch portion 70, wherein the first switch portion 70 comprises a first, second and third electrode 72A, 72B, 72C that are part of the electrical circuitry 38. Those electrodes 72A, 72B, 72C are provided at a first tracker part 16A that also carries the source 22 of electromagnetic radiation.

The first switch 32 further comprises two different second tracker parts 16B1 and 16B2 respectively carrying a second switch portion 74 configured to be electrically coupled to the first switch portion 70 of the first tracker part 16A and a third switch portion 76 configured to be electrically coupled to the first switch portion 70. The second switch portion 74 comprises a first electrical connector 78A and the third switch portion 76 comprises a second electrical connector 78B. FIG. 4B shows the second switch portion 74 when electrically coupled to the first switch portion 70. Since the tracker parts 16A and 16B1 or 16B2 are removable from each other and carry the first, second and third switch portions 70, 74, 76 respectively, the first, second, and third switch portions 70, 74, 76 are also removable from each other.

The two different second tracker parts 16B1 and 16B2 respectively comprise a coupling interface 80A and 80B for coupling the tracker 16 to an object such as patient bone or a surgical instrument (not shown). The first coupling interface 80A exemplarily comprises a clamp that is configured to clamp onto a body part of a patient, such as a vertebra or a tibia. The second coupling interface 80B exemplarily comprises a ring with a biasing screw configured to be coupled to a shaft of a surgical instrument. Of course, both coupling interface 80A, 80B could also be configured identical.

When the first tracker part 16A is mechanically coupled to the second tracker part 16B1 and, thus, the first switch portion 70 is electrically coupled to the second switch portion 74, as can be seen in FIG. 4B, the first electrical connector 78A is arranged offset relative to the three electrodes 72A, 72B, 72C in such a way that the first electrical connector 78A only electrically connects the first and second electrode 72A, 72B, but not the third electrode 72C. Therefore, the first electrical connector 78A closes a portion of the electrical circuitry 38 (only shown schematically in FIGS. 4A, B), which results in the first switch configuration 34 and consequently emission of electromagnetic radiation 24 with the first radiation characteristic 26.

When the first tracker part 16A is mechanically coupled to the second tracker part 16B2 and, thus, the first switch portion 70 is electrically coupled to the third switch portion 76, as can be seen in FIG. 4C, the second electrical connector 78B is arranged offset relative to the three electrodes 72A, 72B, 72C in such a way that the second electrical connector 78B only electrically connects the second and third electrode 72B, 72C, but not the first electrode 72A. Therefore, the second electrical connector 78B closes another portion of the electrical circuitry 38 that is different from the portion of the electrical circuitry 38 closed by the first electrical connector 78A, which results in the second switch configuration 36 and consequently emission of electromagnetic radiation 24 with the second radiation characteristic 28.

As such, prior to a surgical procedure a user can selectively couple the first switch portion 70 (i.e., the first tracker part 16A) with either of the second and third switch portion 74, 76 (i.e., the second tracker part 16B1 or the alternative second tracker part 16B2), which causes the tracker 16 to emit electromagnetic radiation with the first or second radiation characteristics 26, 28 as explained above. The surgical navigation system 10 may have access to an association between the respective object associated with first and second coupling interfaces 80A, 80B and the corresponding first and second radiation characteristic 26, 28. As such, based on the detected radiation characteristic 26, 28 the surgical navigation system 10 can differentiate between the object tracked when the first tracker part 16A is mechanically coupled to the second tracker part 16B1 and the object tracked when the first tracker part 16A is mechanically coupled to the second tracker part 16B1. In case two first tracker parts 16A are provided, different objects can be tracked simultaneously with the navigation system 10 having a priori knowledge of the object being tracked.

The two different second tracker parts 16B1 and 16B2 and, thus, the first and second switch portions 70, 74 shown in FIGS. 4B, C are two separate entities. Alternatively, the second switch portion 74 and the third switch portion 76 are assumed by a single switch portion provided at a single second tracker part (not shown), wherein the single switch portion "activates" the second switch portion 74 when coupled to the first switch portion 70 of the first tracker part 16A for example at a first relative angle (e.g., 0°) and "activates" the third switch portion 76 when coupled to the first switch portion 70 of the first tracker part 16A for example at a second relative angle different than the first relative angle (e.g., 180°). The difference between the first relative angle and the second relative angle can be any angle larger than zero such as 30°, 45°, 90°, 120°, and 180°.

The variant of the first switch described above in the context of FIGS. 4A-C comprises a plurality of electrodes that are selectively connected depending on a position of an electrical connector. Alternatively, the first switch portion 70 may only comprise two electrodes that are configured to be electrically coupled with the second and third switch portion 74, 76, wherein the second and third switch portions 74, 76 differ in electrical characteristics (e.g., an electrical resistance, capacitance, or inductance). For example, the second switch portion 74 may be configured to electrically connect the two electrodes of the first switch portion 70 with a first electrical resistance assigned to the first switch configuration 34 and the second switch portion 74 may be configured to electrically connect the two electrodes with a second resistance assigned to the second switch configuration 36 and different from the first resistance.

Further alternatively, the second and third switch portions 74, 76 may comprise a part of the electrical circuitry 38 that is configured to control the one or more sources 22 of electromagnetic radiation to emit electromagnetic radiation 24 comprising the first or second radiation characteristic 26, 28. For example, when the second switch portion 74 is electrically coupled to the first switch portion 70, electrical circuitries of the first switch portion 70 and the second switch portion 74 form together a combined electrical circuitry configured to control the one or more sources 22 of electromagnetic radiation to emit electromagnetic radiation 24 comprising the first radiation characteristic 26. On the other hand, when the third switch portion 76 is electrically coupled to the first switch portion 70, electrical circuitries of the first switch portion 70 and the third switch portion 76 form together a combined electrical circuitry configured to control the one or more sources 22 of electromagnetic radiation to emit electromagnetic radiation 24 comprising the second radiation characteristic 28.

Figure 5:
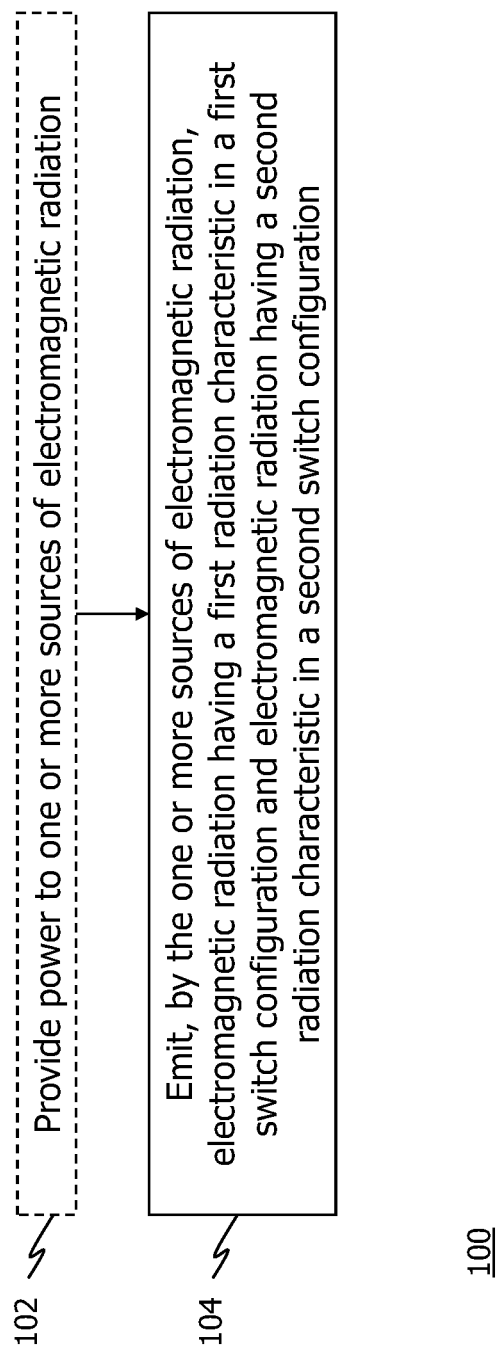
FIG. 5 shows a flowchart of an embodiment of a method for operating the tracker described herein.

FIG. 5 shows a flowchart 100 of an embodiment of a method for operating the tracker 16.

The method may optionally comprise providing power, in step 102, by a power source 30, to the one or more sources 22 of electromagnetic radiation. The method 100 further comprises selectively emitting, in step 104, by the one or more sources 22, electromagnetic radiation 24 having the first radiation characteristic 26 in the first switch configuration 34 and electromagnetic radiation 24 having the second radiation characteristic 28 in the second switch configuration 36. In order to switch between the first and second radiation characteristics 26 and 28, the switch 32 is switched between the first switch configuration 34 and the second switch configuration 26 such as described above.

In some variants of the method, the tracker 16 allows the user to communicate with the surgical navigation system 10 of FIG. 1. As mentioned above, the optical sensor 14 is configured to detect the electromagnetic radiation emitted by the tracker 16. Based on the detected electromagnetic radiation, the processor 12 (or any other computer system communicatively connected with the surgical navigation system 10) is configured to selectively identify (e.g., differentiate between) the first or second switch configuration 34, 36 based on the radiation characteristic detected by the optical sensor 14. The processor 12 may have access to information on the first and second radiation characteristics (such as an operation frequency, wavelength, or geometric arrangement of sources 22 as will be described further below) that allow identifying the switch configuration 34, 36 from the actually detected radiation characteristics. The information may be provided to the processor 12 during manufacturing, maintenance or calibration. The information may be provided in form of one or more predetermined radiation characteristics. As such, the processor 12 may be configured to identify the first or second switch configuration 34, 36 by comparing the detected radiation characteristic with the one or more predetermined radiation characteristics.

The processor 12 may in particular be configured to assign a first tracking mode to the first switch configuration 34 and a second tracking mode to the second switch configuration 36. The first and second tracking modes can be associated with different surgical objects (such as a body part of a patient and an instrument) that the tracker 16 is coupled to. For example, the first tracking mode may be associated to tracking a patient and the second tracking mode may be associated with tracking an instrument.

Alternatively, the first and second tracking mode may be associated with different body parts of the patient. For example, the first tracking mode may be associated with a tibia of a patient and the second mode may be associated with a femur of a patient. In such a case, the user can couple the tracker 16 to the tibia and operate the first switch 32 of the first tracker 16 to switch into the first switch configuration 34. In some implementations, the user can additionally couple a second tracker 16 to the femur of the patient and operate the first switch 32 of the second tracker 16 to switch into the second switch configuration 36. The processor 12 can identify the tracking mode of the respective tracker 16 based on the respective radiation characteristics. The processor 12 may determine based on the identified tracking mode(s) that the first tracker 16 is coupled to the tibia (and, if present, that the second tracker 16 is couple to the femur).

In case a plurality of sources 22 of electromagnetic radiation are provided at a given tracker 16, the processor 12 may determine a position and/or orientation of that tracker 16 and, based thereon, of the surgical object to be tracked by that tracker 16. As an example, the processor 12 may process (e.g., calibrate or visualize) image data of the tibia and/or the femur dependent on a detected position and/or orientation of the respective tracker 16. By setting up the switch configurations of the first and second trackers 16, the user effectively is able to communicate with the processor 12, without having to use a mechanically operated input device of the computer system 18, such as a keyboard or mouse.

The possibilities of the user to communicate with the surgical navigation system 10 are not limited to selecting a certain switch configuration (e.g., pre-operatively). The user may communicate with the surgical navigation system 10 by switching the switch configuration (e.g., during a surgical procedure). To this end, the processor 12 may be configured to specifically identify a switching between the first and second switch configuration 34, 36. The processor 12 may, for example, identify the switching between the first and second switch configuration 34, 36 as a command issued by the user. The command may be related to surgical navigation. For example, the user may switch between the first and second switch configuration 34, 36 in order to instruct the surgical navigation system 10 to perform a certain processing step (e.g., to change a visual representation on a display). The instruction may alternatively be related to other aspects of the surgery such as operation of a surgical instrument (to which the tracker 16 may or may not be attached). For issuing a command, the first switch 32 may be a push button that is biased towards one switch configuration and that only switches to the other switch configuration for the duration the user is operating the first switch 32. For example, the surgical navigation system 10 may activate a suction tube for the duration the surgeon is operating the first switch 32.

It should be noted that the tracker 16 is not limited to providing only two switch configurations. The tracker 16 may have a first switch 32 with three, four, five, six, or more switch configurations. FIGS. 6A-C show a variant of the first switch 32 that has three switch configurations, wherein the first switch configuration (in FIGS. 6A-C the left position of the first switch 32) is assigned to the first radiation characteristic 34 and the second switch configurations (in FIGS. 6A-C the middle position of the first switch 32) is assigned to the second radiation characteristics 28. A third switch configuration (in FIGS. 6A-C the right position of the first switch 32) allows the user to switch off the tracker 16. Alternatively, the tracker 16 may have a separate power switch for switching the tracker 16 on and off. The tracker 16 may be a disposable item, wherein the power switch is operable exactly once to switch on the tracker 16. In such a case, the switch may be switched on by removing a removable isolating material that interrupts a portion of the electrical circuitry 38.

Furthermore, the source 22 of electromagnetic radiation is not limited to selectively assuming a first and second radiation characteristic 26, 28. Alternatively, the source 22 of electromagnetic radiation may be configured to selectively emit electromagnetic radiation with more than two radiation characteristics 26, 28, such as three, four, five, six, or more radiation characteristics. In such a case, the first switch 32 may have a plurality of switch configurations, wherein each switch configuration is assigned to one of the plurality of radiation characteristics. FIGS. 6D-F show an embodiment of a tracker 16, wherein the source 22 of electromagnetic radiation may be configured to selectively emit electromagnetic radiation with three different radiation characteristics and the first switch 32 has three switch configurations, one for each of the three radiation characteristic (and optionally, a fourth switch configuration for switching the tracker 16 on or off).

As will be described further below, a change between the first and second radiation characteristics 24, 26 may not be visible to the user. However, the first and second radiation characteristics 24, 26 are linked to the first and second switch configurations 34, 36. In order to allow the user to easier distinguish between the first and second radiation characteristic 24, 26, the tracker 16 may comprise an indicator configured to provide a first indication to the user in the first switch configuration 34 and a second indication to the user in the second switch configuration 36, wherein the first and second indications are at least one of optically and haptically distinguishable for the user. The user can then identify the first and second radiation characteristics 24, 26 by identifying the related first and second switch configurations 34, 36.

Figure 7B:
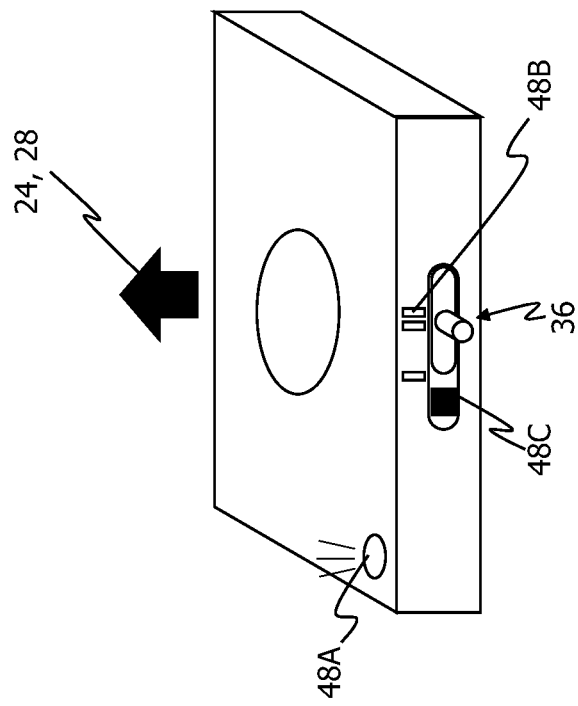
FIG. 7B shows the tracker shown in FIG. 7A with the plurality of indicators providing a second indication in a second switch configuration.
Figure 7A:
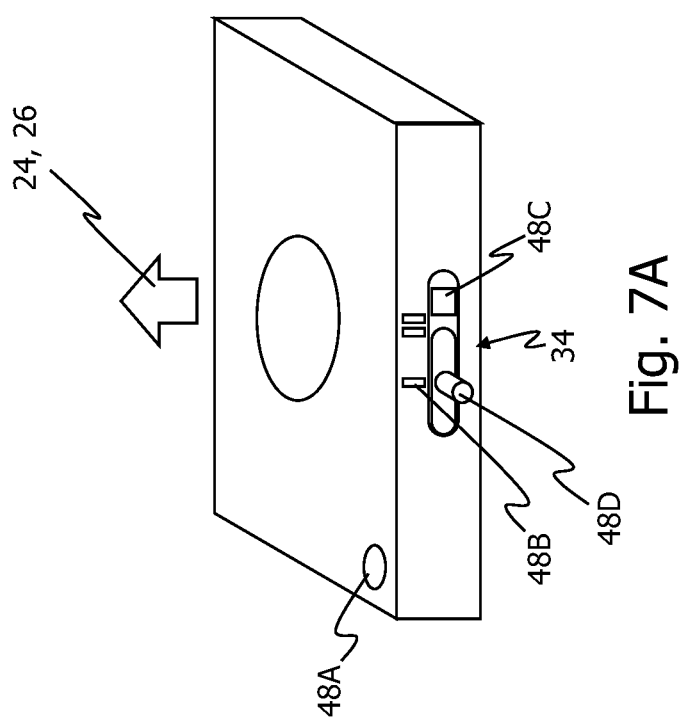
FIG. 7A shows an embodiment of a tracker with a plurality of indicators providing a first indication in a first switch configuration.

In this regard, FIGS. 7A and 7B show a tracker 16 similar to the one of FIGS. 2A and 2B, but with a plurality of indicators 48A, 48B, 48C, 48D configured to provide a first indication in the first switch configuration 34 and a second indication in the second switch configuration 36. In detail, FIG. 7A shows the tracker 16 assuming the first switch configuration 34 and FIG. 7B shows the tracker 16 assuming the second switch configuration 36. FIGS. 7A and 7B show a combination of indicators 48 for the sake of a concise depiction of the indicators 48. However, it should be understood that the tracker 16 may have only one indicator 48 or any combination of indicators 48 described herein.

The tracker 16 shown in FIGS. 7A and 7B comprises an indicator light source 48A configured to emit visible light perceivable by the human eye. The indicator light source 48A is configured to emit light with a first visible wavelength (e.g., a green light) in the first switch configuration 34 and emit light with a second visible wavelength (e.g., a red light) in the second switch configuration 36. Alternatively, the indicator light source 48A may be configured to emit light with a visible wavelength in one of the first and second switch configuration 34, 36 and to emit no light in the other one of the first and second switch configuration 34, 36. Alternatively or additionally, the indicator light source 48A may be configured to operate in a third operation frequency perceivable by the human eye (e.g., 2 Hz) in the first switch configuration and in a fourth operation frequency perceivable by the human eye (e.g., 6 Hz) in the second switch configuration.

The tracker 16 shown in FIGS. 7A and 7B comprises as a further or alternative indicator 48 a first switch position indicator 48B configured to assign a first position of the first switch 32 to the first switch configuration 34 and to assign a second position of the first switch 32 to the second switch configuration 36. The first switch position indicator 48B shown in FIGS. 7A and 7B comprises a numbering in Roman numerals. Alternatively, the first switch position indicator 48B may comprise different symbols and/or terms (e.g., describing different tracking modes). For example, the first switch position indicator 48B may comprise terms that indicate whether the tracker 16 is coupled to an instrument or a patient (e.g., with the terms "instrument" and "patient", or "I" and "P"). Further alternatively, the first switch position indicator 48B may comprise terms that indicate anatomical parts of the patient that the tracker 16 is coupled to (e.g., with the terms "tibia" and "femur", or "T" and "F"). The first switch position indicator 48B may be formed raised or recessed relative to a surrounding region of the tracker 16 in order to be haptically distinguishable for the user.

The tracker 16 shown in FIGS. 7A and 7B comprises as a further or alternative indicator 48 a second switch position indicator 48C configured to display a first symbol in the first switch configuration 34 and a second symbol in the second switch configuration 36. In the example shown in FIGS. 7A and 7B, the first symbol is a white square and the second symbol is a black square. Alternatively, the first and second symbol may be any other set of symbols that are optically distinguishable for the user. The first switch 32 covers the second symbol in the first switch configuration 34 and uncovers the second symbol in the second switch configuration 36. Similarly, the first symbol is covered by the first switch 32 in the second switch configuration 36 and uncovered in the first switch configuration. Therefore, the first symbol is visible to the user in the first switch configuration 34 and the second symbol is visible to the user in the second switch configuration 36. Evidently, one of the two symbols may be omitted, so that only a single symbol, when being uncovered, provides discrete visual feedback to the user.

The tracker 16 shown in FIGS. 7A and 7B comprises as a still further or alternative indicator 48 a haptic switch feature 48D. The haptic switch feature 48D enables the user an easier operation of the first switch 32 and allows the user to haptically determine the switch configuration of the first switch 32 (e.g., with reference to another haptic feature that remains stationary).

In the following, different embodiments of specific radiation characteristics are described. The different radiation characteristics are not exclusive to each other and may therefore be combined in any combination.

In one example, the first radiation characteristic 26 comprises emission of electromagnetic radiation 24 at a first operation frequency and the second radiation characteristic 28 comprises emission of electromagnetic radiation at a second operation frequency different from the first operation frequency. The first and second operation frequencies each indicate a rate of a periodic intensity change of the electromagnetic radiation 24. The frequencies and rates may be visually distinguishable (e.g., be selected to fall within a range of 0.5 Hz to 20 Hz, or to correspond to a continuous radiation emission) FIG. 8A shows in a time diagram an intensity change of the electromagnetic radiation 24 at a first operation frequency. As can be seen, the intensity periodically alternates between a higher intensity and a lower intensity. The operation frequency may be defined by a time duration between two points of time at which the intensity switches from the lower intensity to the higher intensity.

The lower intensity shown in FIG. 8A is larger than zero. Alternatively, the lower intensity can be zero (or essentially zero). FIG. 8B shows in a time diagram an intensity change of the electromagnetic radiation 24 at the first operation frequency, wherein the intensity alternates between an intensity of zero and an intensity that is larger than zero. A source 22 of electromagnetic radiation operating at such an operation frequency alternates between emitting light and not emitting light at the operation frequency.

FIG. 8C shows in a time diagram a change of the intensity of the electromagnetic radiation 24 from the first operation frequency 40 to a second operation frequency. In the example shown in FIG. 8C, the first operation frequency 40 is smaller than the second operation frequency 42. Alternatively, the first operation frequency 40 may be higher than the second operation frequency 42.

The change of the operation frequency can be caused by the user switching the switch configuration as described in the following. Initially, the switch 32 is set in the first switch configuration 34 (see, e.g., FIG. 2A). The electrical circuitry 38 is configured to selectively control the (at least one) source 22 of electromagnetic radiation to emit electromagnetic radiation 24 at the first operation frequency 40 in the first switch configuration 34. The user then operates the switch 32 to switch from the first switch configuration 34 to the second switch configuration 36 (see, e.g., FIG. 2B). Thereupon, the electrical circuitry 38 is configured to selectively control the (at least one) source 22 of electromagnetic radiation to emit electromagnetic radiation 24 having the second operation frequency 42.

FIG. 8C shows a single change of the radiation characteristic. Such a change may be signalled with a switch 32 that permanently remains in the second switch configuration 36, such as the one explained above. The user can subsequently use the tracker 16 while the at least one source 22 of electromagnetic radiation emits electromagnetic radiation 24 with the second radiation characteristic, i.e., at the second operation frequency 42.

The radiation characteristic may be changed multiple times, such as twice, thrice or, four times during a surgical procedure. The time diagram of FIG. 8D shows a first change 44 of the intensity of the electromagnetic radiation 24 from the first operation frequency 40 to the second operation frequency 42 followed by a second change 46 back to the first operation frequency 40. In essence, the radiation characteristic 24 initially comprises the first operation frequency 40 and temporally switches to the second operation frequency 42.

The change of the radiation characteristic 24 may be performed with a switch 32 that permanently remains in a switch configuration after being operated such as the one shown in FIG. 2A. Alternatively, the radiation characteristic 24 may be changed using a switch 32 that only temporarily switches to the second switch configuration for the duration the user is operating the switch 32 (or for a fixed time duration after the switch 32 was operated by the user).

The second operation frequency 42 shown in FIGS. 8C and 8D is an operation frequency that is larger than zero. Alternatively, the second operation frequency 42 (or the first operation frequency 40) may be zero (or, conversely, infinite), corresponding to a continuous emission of electromagnetic radiation 24. The intensity of electromagnetic radiation 24 during the continuous emission may be equal to the larger intensity of the first operation frequency 40 as shown in FIG. 8E. Alternatively, the intensity may be smaller in order to reduce power consumption.

The optical sensor 14 discussed above with reference to FIG. 1 (such as the camera described above) may have a frame rate that is larger (e.g., two times or three times larger) than a larger one of the first and second operation frequencies 40, 42 of the tracker 16. An optical sensor 14 having such a frame rate has a better probability of properly resolving the first and second operation frequencies 40, 42 and, therefore, increases the accuracy of the surgical navigation system 10.

As explained above, one way the first and second radiation characteristics 26, 28 may differ is in the operation frequency. Additionally or alternatively, the first radiation characteristic 26 may comprise emission of electromagnetic radiation having a first wavelength and the second radiation characteristic 28 comprises emission of electromagnetic radiation having a second wavelength different from the first wavelength. The first wavelength and the second wavelength may be within the visible spectrum (e.g., red and green or white and blue). The user can then easily differentiate between the first and second radiation characteristics 26, 28 based on the colour of the light emitted by the at least one source 22 of electromagnetic radiation. Alternatively, the first and second wavelengths may be outside the visible spectrum, such as in the infrared spectrum. Such a tracker 16 is less distracting to the user and less affected by ambient lighting.

The tracker 16 shown in FIG. 2A only comprises a single source 22 of electromagnetic radiation 24. However, as said, the tracker 16 is not limited to a single source 22 of electromagnetic radiation. Alternatively, the tracker 16 may comprise a plurality of sources 22 of electromagnetic radiation such as two, three, four, five, six, or more sources 22 of electromagnetic radiation. The electrical circuitry 38 may be configured to selectively control the plurality of sources 22 of electromagnetic radiation in unison to emit electromagnetic radiation 24 having the first radiation characteristic 26 in the first switch configuration 34 and to emit electromagnetic radiation 24 having the second radiation characteristic 28 in the second switch configuration 36. For example, when the first switch 32 switches from the first switch configuration 34 to the second switch configuration 36, all sources 22 of electromagnetic radiation emit light at the second operation frequency 42 and/or the second wavelength.

Alternatively or additionally, changing between the first and second radiation characteristics 26, 28 of the plurality of sources 22 of electromagnetic radiation may comprise at least one of (i) at least one of the sources 22 of electromagnetic radiation starting emitting electromagnetic radiation 24 and (ii) at least one of the sources 22 of electromagnetic radiation stopping emitting electromagnetic radiation 24.

FIGS. 9A and 9B show an embodiment of a tracker 16 with multiple (here: three) sources 22 of electromagnetic radiation that can be controlled individually or in sets to stop, continue, or start emitting electromagnetic radiation 24. That is, the tracker 16 comprises a first source 22A, a second source 22B, and a third source 22C of electromagnetic radiation (and, optionally, a fourth source). As can be seen in FIG. 9A, when the first switch 32 is in the first switch configuration 34, the electrical circuitry 38 is configured to selectively control the plurality of sources 22 of electromagnetic radiation to emit electromagnetic radiation 24 having the first radiation characteristic 26, wherein the first radiation characteristic 26 comprises the first and second sources 22A, 22B of electromagnetic radiation emitting electromagnetic radiation and the third source 22C of electromagnetic radiation not emitting electromagnetic radiation.

As can be seen in FIG. 9B, once the first switch 32 switches from the first switch configuration 34 to the second switch configuration 36, the electrical circuitry 38 is configured to selectively control the plurality of sources 22 of electromagnetic radiation to emit electromagnetic radiation 24 having the second radiation characteristic 26, wherein the first source 22A of electromagnetic radiation stops emitting electromagnetic radiation, the second source 22B of electromagnetic radiation continues emitting electromagnetic radiation, and the third source 22C of electromagnetic radiation stops emitting electromagnetic radiation.

The second source 22B of electromagnetic radiation is spaced further apart from the third source 22C of electromagnetic radiation than from the first source 22A of electromagnetic radiation. The two sources 22B, 22C emitting electromagnetic radiation in the second radiation characteristic 28 are arranged in a different orientation and distance relative to each other compared to the two sources 22A, 22B emitting electromagnetic radiation in the first radiation characteristic 26. Therefore, the second radiation characteristic 26 differs geometrically from the first radiation characteristic 24. By operating the first switch 32, the user can effectively change a geometrical pattern of sources 22 of electromagnetic radiation that emit electromagnetic radiation 24.

In some variants, a fourth or fifth source 22 of electromagnetic radiation may be provided. The plurality of sources 22 of electromagnetic radiation may then be controlled such that at least (e.g., exactly) three sources 22 of electromagnetic radiation are emitting with the same radiation characteristic 26, 28 (e.g., are simultaneously on) in each switch configuration 34, 36.

FIGS. 10A and 10B show another variant of a tracker 16 comprising eight sources 22 of electromagnetic radiation. In the first switch configuration 34 shown in FIG. 10A, three sources 22 of electromagnetic radiation emit electromagnetic radiation 24 (which is denoted in FIG. 10A as white filled circles). Five sources 22 of electromagnetic radiation do not emit electromagnetic radiation 24 (which is denoted in FIG. 10A with black filled circles). The tracker 16 has a lower power consumption while in the first switch configuration 34.

In the second switch configuration 36 shown in FIG. 10B, all eight sources 22 of electromagnetic radiation emit electromagnetic radiation 24. A position and/or orientation of the tracker 16 can be determined more accurately by the surgical navigation system 10 while the tracker 16 is in the second switch configuration 36.

The trackers 16 described above comprise one switch 32. However, the tracker 16 is not limited to a single switch 32. Alternatively, the tracker 16 may comprise a plurality of switches.

FIGS. 11A to 11D show a variant of a tracker 16 with a plurality of sources 22 of electromagnetic radiation, a first switch 32 and a second switch 50. The tracker 16 has six sources 22A-F of electromagnetic radiation. A first subset 52 comprises a first and second source 22A, 22B of electromagnetic radiation that is assigned to the first switch 32. A second subset 54 comprises a third and fourth source 22C, 22D of electromagnetic radiation that is assigned to the second switch 50.

Figure 11A:
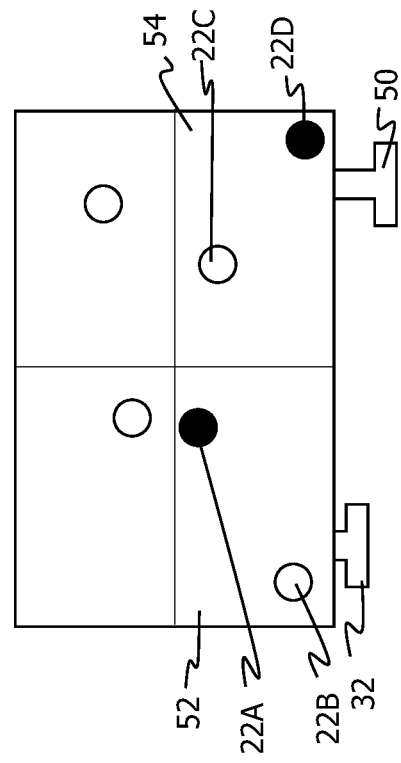
FIG. 11A shows an embodiment of a tracker with a first switch and a second switch emitting a first radiation characteristic.
Figure 11B:
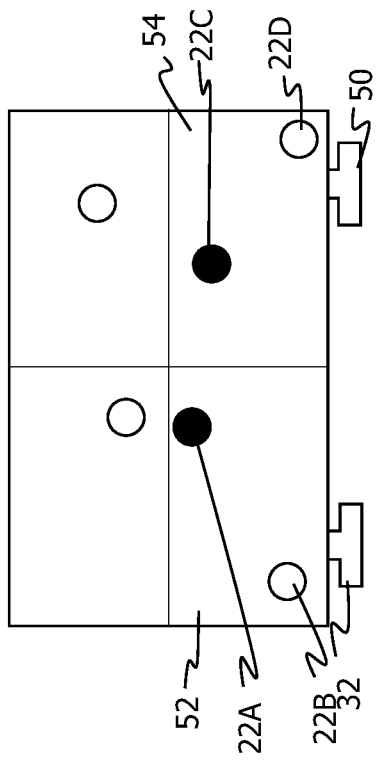
FIG. 11B shows the tracker shown in FIG. 11A emitting a second radiation characteristic.
Figure 11C:
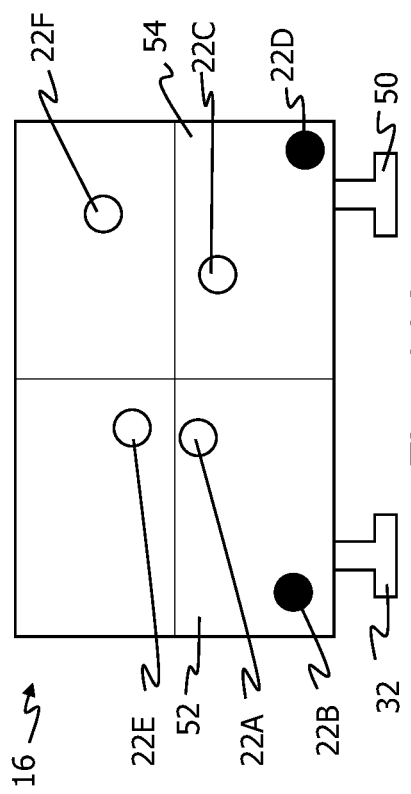
FIG. 11C shows the tracker shown in FIG. 11A emitting a third radiation characteristic.
Figure 11D:
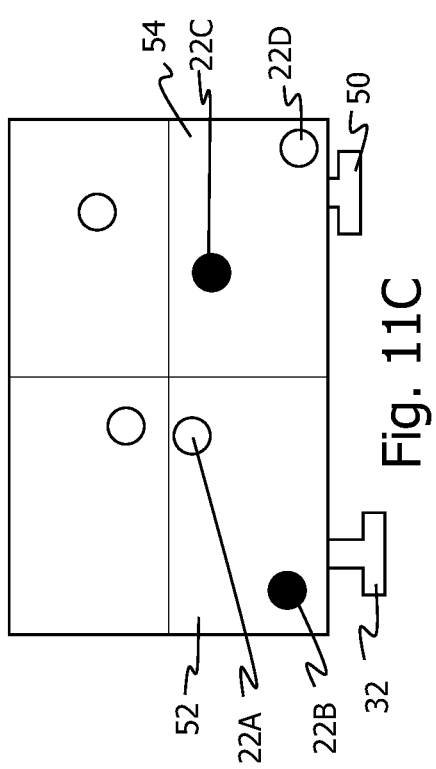
FIG. 11D shows the tracker shown in FIG. 11A emitting a fourth radiation characteristic.

The switch 32 is configured to be operated by the user between a first switch configuration (shown in FIGS. 11A and 11C) and a second switch configuration (shown in FIGS. 11B and 11D). The further switch 50 is configured to be operated by the user between a third switch configuration (shown in FIGS. 11A and 11B) and a fourth switch configuration (shown in FIGS. 11C and 11D).

The first subset 52 of the plurality of sources 22 of electromagnetic radiation is configured to selectively emit electromagnetic radiation 24 having a first partial radiation characteristic or a second partial radiation characteristic. The first partial radiation characteristic comprises the first source 22A of electromagnetic radiation emitting electromagnetic radiation and the second source 22B of electromagnetic radiation not emitting electromagnetic radiation, as shown in FIGS. 11A and 11C. The second partial radiation characteristic comprises the first source 22A of electromagnetic radiation not emitting electromagnetic radiation and the second source 22B of electromagnetic radiation emitting electromagnetic radiation, as shown in FIG. 11B. In essence, the first and second partial radiation characteristics differ in whether the first source 22A or the second source 22B is emitting electromagnetic radiation.

The second subset 54 of the plurality of sources 22 of electromagnetic radiation is configured to selectively emit electromagnetic radiation 24 having a third partial radiation characteristic or a fourth partial radiation characteristic. The third partial radiation characteristic comprises the third source 22C of electromagnetic radiation emitting electromagnetic radiation and the fourth source 22D of electromagnetic radiation not emitting electromagnetic radiation, as shown in FIG. 11A. The fourth partial radiation characteristic comprises the third source 22C of electromagnetic radiation not emitting electromagnetic radiation and the fourth source 22D of electromagnetic radiation emitting electromagnetic radiation as shown in FIG. 11C. Again, the third and fourth partial radiation characteristics differ in whether the third source 22C or fourth source 22D is emitting electromagnetic radiation.

The two switches 32, 50 are configured to be operated by the user to only change the partial radiation characteristic of each assigned subset 52, 54 of sources 22A-D of electromagnetic radiation. Therefore, the user can operate the first switch 32 in order to change the partial radiation characteristic of the first subset 52 without changing the partial radiation characteristic of the second subset 52. Vice versa, the user can operate the second switch 50 in order to change the partial radiation characteristic of the second subset 54 without changing the partial radiation characteristic of the first subset 52.

The radiation characteristic 24 of the entire tracker 16 comprises the partial radiation characteristic of each subset 52, 54. Since each subset 52, 54 can switch between two partial radiation characteristics, the tracker 16 has four radiation characteristics that are shown in FIGS. 11A-D. FIG. 11A shows the tracker 16 with a first radiation characteristics comprising the first partial radiation characteristic of the first subset 52 and the third partial radiation characteristic of the second subset 54. FIG. 11B shows the tracker 16 with a second radiation characteristics comprising the second partial radiation characteristic of the first subset 52 and the third partial radiation characteristic of the second subset 54. FIG. 11C shows the tracker 16 with a third radiation characteristics comprising the first partial radiation characteristic of the first subset 52 and the fourth partial radiation characteristic of the second subset 54. FIG. 11D shows the tracker 16 with a fourth radiation characteristics comprising the second partial radiation characteristic of the first subset 52 and the fourth partial radiation characteristic of the second subset 54.

The sources of radiation 22E and 22F may in some variants be included in the first subset 52, and the second subset 54, respectively. In some variants, the sources 22E and 22F can be omitted.

Figure 12B:
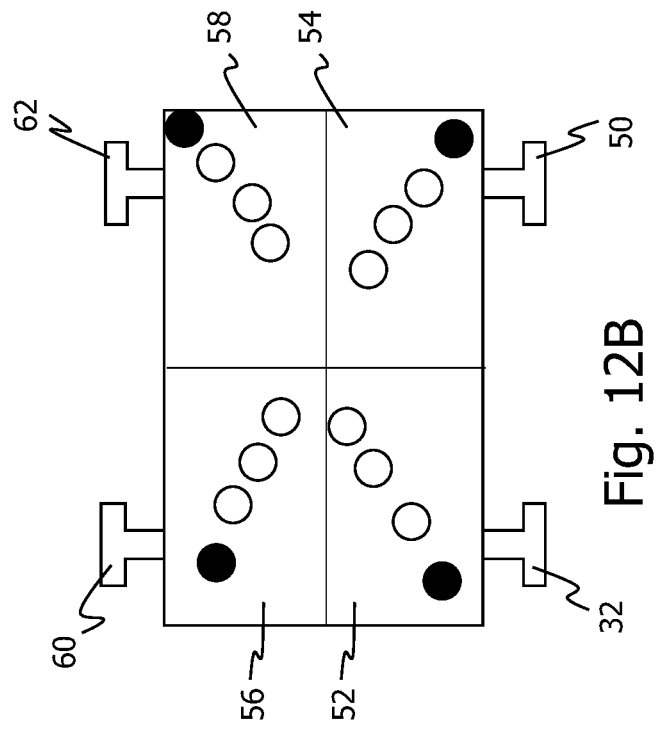
FIG. 12B shows an embodiment of a tracker with four subsets each with four of sources of electromagnetic radiation.
Figure 12A:
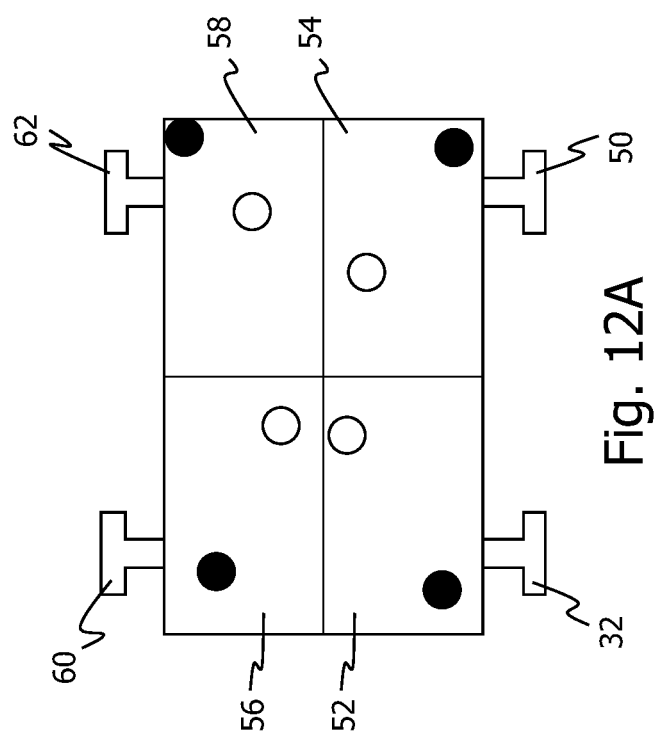
FIG. 12A shows an embodiment of a tracker with four subsets of sources of electromagnetic radiation and four switches.

The tracker 16 shown in FIGS. 11A-D comprises two subsets of sources 22 of electromagnetic radiation. Alternatively, the tracker 16 may comprise more than two subsets of sources 22 of electromagnetic radiation. FIG. 12A shows a tracker 16 with four subsets 52, 54, 56, 58 of sources 22 of electromagnetic radiation and four switches 32, 50, 60, 62. Each switch 32, 50, 60, 62 is assigned to one of the four subsets 52, 54, 56, 58 and allows switching between two partial radiation characteristics of each assigned subset 52, 54, 56, 58. The radiation characteristic 24 of the entire tracker 16 comprises the partial radiation characteristic of each subset 52, 54, 60, 62 and, therefore, comprises sixteen different radiation characteristics.

The subsets of the trackers 16 shown in FIGS. 11A-D and 12A each comprise exactly two sources 22 of electromagnetic radiation, wherein each subset can change between two different partial radiation characteristics. Alternatively, the tracker 16 may comprise subsets with more than two (e.g., three, four or more) sources 22 of electromagnetic radiation and/or subsets each with more than two (e.g., three, four or more) different partial radiation characteristics. FIG. 12B shows a variant of a tracker 16 with four subsets 52, 54, 56, 58 each with four of sources 22 of electromagnetic radiation, and four switches 32, 50, 60, 62 each assigned to one of the corresponding subsets 52, 54, 56, 58. Furthermore, each switch 32, 50, 60, 62 has four switch configurations that allows selecting one source 22 of electromagnetic radiation of the assigned subsets 52, 54, 56, 58 to emit electromagnetic radiation.

For the subsets described above, each partial radiation characteristic comprises exactly one source 22 of electromagnetic radiation emitting electromagnetic radiation, while the remaining sources 22 of electromagnetic radiation of the subset do not emit electromagnetic radiation. Therefore, changing the partial radiation characteristic essentially changes which single source 22 of the subset is emitting electromagnetic radiation. However, a partial radiation characteristic may not only comprise a single source 22 of electromagnetic radiation emitting electromagnetic radiation. A partial radiation characteristic may comprise multiple (e.g., three, four or more) sources 22 of the associated subset emitting electromagnetic radiation.

Consequently, changing a partial radiation characteristic may comprise a plurality of sources 22 of the associated subset stopping or continuing to emit electromagnetic radiation.

It is noted that the sources 22 of electromagnetic radiation for the trackers 16 shown in FIGS. 10 and 11 are preferably arranged asymmetrically in order to prevent a ambiguous orientations and/or positions of the trackers 16 while tracking. Furthermore, the sources 22 of electromagnetic radiation are preferably arranged in such a way that any geometrical arrangement of the sources 22 of electromagnetic radiation that can be the result of different switch configurations is also asymmetrical. The sources 22 of electromagnetic radiation may also be arranged in such a way that any geometrical arrangement of the sources 22 of electromagnetic radiation that can be the result of different switch configurations is unique.

The features described in relation to the exemplary embodiments shown in the drawings can be readily combined to result in different embodiments. It is apparent, therefore, that the present disclosure may be varied in many ways. Such variations are not to be regarded as a departure from the scope of the invention as defined by the claims appended hereto.

The invention claimed is:

1. A tracker for a surgical navigation system, the tracker comprising:
a first switch configured to be operated between a first switch configuration and a second switch configuration;
one or more sources of electromagnetic radiation configured to selectively emit electromagnetic radiation with a first radiation characteristic or a second radiation characteristic; and
electrical circuitry configured to selectively control the one or more sources of electromagnetic radiation to emit electromagnetic radiation having the first radiation characteristic in the first switch configuration and to emit electromagnetic radiation having the second radiation characteristic in the second switch configuration, wherein the second radiation characteristic is different from the first radiation characteristic, wherein the first switch comprises:
a first switch portion;
a second switch portion configured to be electrically coupled to the first switch portion; and
a third switch portion configured to be electrically coupled to the first switch portion,
wherein the first switch is in the first switch configuration when the second switch portion is electrically coupled to the first switch portion and in the second switch configuration when the third switch portion is electrically coupled to the first switch portion, and
wherein the tracker comprises a first tracker part and at least one second tracker part that is one of movable relative to and removable from the first tracker part, wherein the first switch portion is provided at the first tracker part and the second switch portion and the third switch portion are collectively or individually provided at the at least one second tracker part.

2. The tracker according to claim 1, wherein the first radiation characteristic comprises emission of electromagnetic radiation at a first operation frequency and the second radiation characteristic comprises emission of electromagnetic radiation at a second operation frequency different from the first operation frequency, wherein the first and second operation frequencies each indicate a rate of a periodic intensity change of the electromagnetic radiation.

3. The tracker according to claim 2, wherein one of the first operation frequency and the second operation frequency is zero with a continuous emission of electromagnetic radiation.

4. The tracker according to claim 1, wherein the first radiation characteristic comprises emission of electromagnetic radiation having a first wavelength and the second radiation characteristic comprises emission of electromagnetic radiation having a second wavelength different from the first wavelength.

5. The tracker according to claim 1, wherein the tracker comprises a plurality of sources of electromagnetic radiation, and the plurality of sources of electromagnetic radiation are configured to change between the first and second radiation characteristics, wherein, for changing between the first and second radiation characteristics at least one of:
at least one of the sources of electromagnetic radiation is configured to start emitting electromagnetic radiation, and at least one of the sources of electromagnetic radiation is configured to stop emitting electromagnetic radiation.

6. The tracker according to claim 5, wherein:
a first subset of sources of electromagnetic radiation comprises exactly two sources of electromagnetic radiation, and
in the first radiation characteristic only one source of the first subset is configured to emit electromagnetic radiation, and in the second radiation characteristic only the other source of the first subset is configured to emit electromagnetic radiation.

7. The tracker according to claim 5, further comprising:
a second switch configured to be operated between a third switch configuration and a fourth switch configuration,
wherein a first subset of the plurality of sources of electromagnetic radiation is assigned to the first switch and a second subset of the plurality of sources of electromagnetic radiation is assigned to the second switch,
wherein the first subset of the plurality of sources of electromagnetic radiation is configured to selectively emit electromagnetic radiation having a first partial radiation characteristic or a second partial radiation characteristic, and wherein the second subset of the plurality of sources of electromagnetic radiation is configured to selectively emit electromagnetic radiation having a third partial radiation characteristic or a fourth partial radiation characteristic, and
wherein the first and second switches are configured to be operated to only change the partial radiation characteristic of each assigned subset of the sources of electromagnetic radiation.

8. The tracker according to claim 1, wherein the tracker comprises an indicator configured to provide a first indication in the first switch configuration and a second indication in the second switch configuration, wherein the first indication and second indication are at least one of optically and haptically distinguishable for a user.

9. The tracker according to claim 1, wherein the first switch is pre-configured to assume the first switch configuration and adapted to switch from the first to the second switch configuration only for a duration that the first switch is operated or for a fixed time duration after the first switch was operated.

10. The tracker according to claim 1, further comprising one of a power source and a wireless power reception device.

11. The tracker according to claim 1, further comprising one or more passive tracking elements configured to reflect electromagnetic radiation.

12. The tracker according to claim 1, wherein the first switch has more than two switch configurations, and wherein the one or more sources of electromagnetic radiation are configured to selectively emit electromagnetic radiation with a number of radiation characteristics at least equal to the number of switch configurations, wherein each of the switch configurations is assigned to one of the radiation characteristics.

13. The tracker according to claim 1, wherein the first switch comprises a mechanical switch configured to be operated by a user.

14. The tracker according to claim 1, wherein one of the first and the at least one second tracker part carries the one or more sources of electromagnetic radiation, and wherein the other of the first and the at least one second tracker part comprises an interface for coupling the tracker to an object that is to be tracked.

15. A surgical navigation system comprising:
a tracker comprising a first switch configured to be operated between a first switch configuration and a second switch configuration, the tracker further comprising one or more sources of electromagnetic radiation configured to selectively emit electromagnetic radiation with a first radiation characteristic or a second radiation characteristic, and electrical circuitry configured to selectively control the one or more sources of electromagnetic radiation to emit electromagnetic radiation having the first radiation characteristic in the first switch configuration and to emit electromagnetic radiation having the second radiation characteristic in the second switch configuration, wherein the second radiation characteristic is different from the first radiation characteristic, wherein the first switch comprises:
a first switch portion;
a second switch portion configured to be electrically coupled to the first switch portion; and
a third switch portion configured to be electrically coupled to the first switch portion,
wherein the first switch is in the first switch configuration when the second switch portion is electrically coupled to the first switch portion and in the second switch configuration when the third switch portion is electrically coupled to the first switch portion, and
wherein the tracker comprises a first tracker part and at least one second tracker part that is one of movable relative to and removable from the first tracker part, wherein the first switch portion is provided at the first tracker part and the second switch portion and the third switch portion are collectively or individually provided at the at least one second tracker part;
an optical sensor capable of detecting different radiation characteristics of the tracker; and
a processor configured to selectively identify the first or second switch configuration based on the radiation characteristic detected by the optical sensor.

16. The surgical navigation system according to claim 15, wherein the processor is configured to assign a first tracking mode to the first switch configuration and a second tracking mode to the second switch configuration.

17. The surgical navigation system according to claim 16, wherein the first radiation characteristic comprises emission of electromagnetic radiation at a first operation frequency and the second radiation characteristic comprises emission of electromagnetic radiation at a second operation frequency different from the first operation frequency, wherein the first operation frequency and the second operation frequency each indicate a rate of a periodic intensity change of the electromagnetic radiation, and wherein the optical sensor is a camera having a frame rate that is at least two times larger than a larger one of the first operation frequency and the second operation frequency of the tracker.

18. The surgical navigation system according to claim 15, wherein the first radiation characteristic comprises emission of electromagnetic radiation at a first operation frequency and the second radiation characteristic comprises emission of electromagnetic radiation at a second operation frequency different from the first operation frequency, wherein the first operation frequency and the second operation frequency each indicate a rate of a periodic intensity change of the electromagnetic radiation, and wherein the optical sensor is a camera having a frame rate that is at least two times larger than a larger one of the first operation frequency and the second operation frequency of the tracker.

19. A method for operating a tracker for a surgical navigation system, the tracker comprising a first switch configured to be operated between a first switch configuration and a second switch configuration, one or more sources of electromagnetic radiation, and electrical circuitry configured to selectively control the one or more sources of electromagnetic radiation to emit electromagnetic radiation with a first radiation characteristic or a second radiation characteristic, wherein the second radiation characteristic is different from the first radiation characteristic, wherein the first switch comprises a first switch portion, a second switch portion configured to be electrically coupled to the first switch portion, and a third switch portion configured to be electrically coupled to the first switch portion, wherein the first switch is in the first switch configuration when the second switch portion is electrically coupled to the first switch portion and in the second switch configuration when the third switch portion is electrically coupled to the first switch portion, and, wherein the tracker comprises a first tracker part and at least one second tracker part that is one of movable relative to and removable from the first tracker part, wherein the first switch portion is provided at the first tracker part and the second switch portion and the third switch portion are collectively or individually provided at the at least one second tracker part, wherein the method comprises:

emitting, by the one or more sources of electromagnetic radiation, electromagnetic radiation having the first radiation characteristic in the first switch configuration;

operating the switch so as to switch from the first switch configuration to the second switch configuration; and emitting, by the one or more sources of electromagnetic radiation, electromagnetic radiation having the second radiation characteristic in the second switch configuration.

* * * * *